(12) United States Patent
Hu et al.

(10) Patent No.: US 12,733,938 B2
(45) Date of Patent: Sep. 15, 2026

(54) HEMOSTATIC CLIP WITH SPLIT STRUCTURE

(71) Applicant: ZHEJIANG SOUDON MEDICAL TECHNOLOGY CO., LTD., Hangzhou (CN)

(72) Inventors: Xiaogang Hu, Hangzhou (CN); Ruchun Zhou, Hangzhou (CN)

(73) Assignee: ZHEJIANG SOUDON MEDICAL TECHNOLOGY CO., LTD., Hangzhou (CN)

( * ) Notice: Subject to any disclaimer, the term of this patent is extended or adjusted under 35 U.S.C. 154(b) by 294 days.

(21) Appl. No.: 18/294,619

(22) PCT Filed: Dec. 28, 2023

(86) PCT No.: PCT/CN2023/142591

§ 371 (c)(1),
(2) Date: Feb. 2, 2024

(87) PCT Pub. No.: WO2024/146435

PCT Pub. Date: Jul. 11, 2024

(65) Prior Publication Data

US 2024/0423636 A1 Dec. 26, 2024

(30) Foreign Application Priority Data

Jan. 4, 2023 (CN) ......................... 202310007981.1

(51) Int. Cl.
*A61B 17/122* (2006.01)
*A61B 17/00* (2006.01)

(52) U.S. Cl.
CPC .... *A61B 17/122* (2013.01); *A61B 2017/0046* (2013.01)

(58) Field of Classification Search
CPC .... A61B 2017/099; A61B 2017/00296; A61B 2017/00367; A61B 2017/00862; A61B 2017/00358; A61B 2017/0046; A61B 2017/00477; A61B 2017/00526; A61B 17/00234; A61B 17/083; A61B 17/08; A61B 17/10; A61B 17/22
USPC ................ 606/155, 153, 151, 157, 143, 142
See application file for complete search history.

(56) References Cited

FOREIGN PATENT DOCUMENTS

CN 113425362 A * 9/2021 ......... A61B 17/1227

* cited by examiner

*Primary Examiner* — Jocelin C Tanner
(74) *Attorney, Agent, or Firm* — LANWAY IPR SERVICES; Chun-Ming Shih

(57) ABSTRACT

The invention provides a hemostatic clip with a split structure, which includes a control portion and a releaser. The control portion includes a grip, a handle, a spring tube, a mandrel, a clamp with a barb at the end, and an internal socket. The releaser includes a middle ring and an outer ring. The handle is connected with the outer ring through the spring tube. The outer ring is sleeved on the outside of the middle ring, and an inner side of the outer ring and an outer side of the middle ring are provided with a first limiting mechanism that limits a radial movement of the middle ring toward a proximal end. The middle ring is provided with a tightening tube. A distal end passes through the outer ring, the middle ring and the tightening tube in sequence, and then is connected with the clamp through the internal socket.

9 Claims, 6 Drawing Sheets

HEMOSTATIC CLIP WITH SPLIT STRUCTURE

FIELD OF THE INVENTION

The invention relates to the field of medical auxiliary devices, in particular to a release portion of a hemostatic clip used with an endoscope.

BACKGROUND OF THE INVENTION

Endoscopic hemostasis is an important treatment method for the treatment of gastrointestinal bleeding. Currently, commonly used endoscopic hemostasis methods include laser coagulation, electrocoagulation, local injection of drugs, drug spraying, and hemostatic clamping.

The hemostatic clamping method is the most effective and clinically valuable method for the non-surgical treatment of gastrointestinal bleeding at the current stage due to its small trauma, fast hemostasis, low incidence of re-bleeding, few complications, and accurate efficacy.

For the medical devices used in the hemostatic clamping method, there is a clinical need for a clip device that can flexibly adjust the clamping angle, can be released simply, and can be opened again after release.

However, the above hemostatic clip products are used in a small environment inside the human body, and their composition needs to be integrated (too many and complex assembly structures can easily cause parts to fall, causing medical accidents); existing production methods generally use CNC machining, so that as a consumable part, the tightening tube (which will remain in the body together with the clip for a period of time) is extremely expensive. Meanwhile, the technical solution solves the problems in assembly. Due to the processing method of current CNC machined parts, the principle of "small into large" must be followed during assembly, but it can be "fitted in" first and then welded through the split structure of the technical solution, which solves the problems in assembly.

BRIEF SUMMARY OF THE DISCLOSURE

In order to solve the above technical problems, the invention provides a hemostatic clip with a split structure that is simple in structure and cheap in cost, which includes a control portion and a releaser, the control portion including a grip, a handle, a spring tube, a mandrel, a clamp with a barb at the end, and an internal socket, the grip being connected with the mandrel, wherein the releaser includes a middle ring and an outer ring; the handle is connected with the outer ring through the spring tube; the outer ring is sleeved on the outside of the middle ring, and an inner side of the outer ring and an outer side of the middle ring are provided with a first limiting mechanism that limits a radial movement of the middle ring toward a proximal end; the middle ring is provided with a tightening tube; a distal end of the mandrel passes through the outer ring, the middle ring and the tightening tube in sequence, and then is connected with the clamp through the internal socket; the internal socket and the clamp are located in the tightening tube, and the middle ring is provided inside with a second limiting mechanism that limits a radial movement of the internal socket toward the proximal end.

As an improvement of the hemostatic clip with a split structure according to the invention, the middle ring includes a middle ring front portion and a middle ring rear portion; an inner side of the middle ring front portion is provided with an inner connecting ring to form the first limiting mechanism; an outer side of the middle ring front portion is provided with an outer connecting ring, which forms the second limiting mechanism together with a protrusion provided on an inner side of a proximal end of the outer ring; the middle ring rear portion is fixedly connected with the tightening tube.

As an improvement of the hemostatic clip with a split structure according to the invention, a maximum force of 30 N may be withstood between the middle ring front portion and the middle ring portion.

As an improvement of the hemostatic clip with a split structure according to the invention, the middle ring front portion is provided with a C-shaped port; relative to the C-shaped port, a V-shaped elastic piece is provided at the middle ring rear portion; an opening position of the V-shaped elastic piece is inserted into the C-shaped port.

As an improvement of the hemostatic clip with a split structure according to the invention, the middle ring rear portion is provided with a C-shaped port; relative to the C-shaped port, a V-shaped elastic piece is provided at the middle ring front portion; an opening position of the V-shaped elastic piece is inserted into the C-shaped port.

As an improvement of the hemostatic clip with a split structure according to the invention, the tightening tube is of a cylindrical structure with a hollow center, which has a distal end provided with a third limiting mechanism that limits the clamp from running out and a proximal end provided with a fourth limiting mechanism that limits a position of the clamp after clamping.

As an improvement of the hemostatic clip with a split structure according to the invention, the third limiting mechanism is two limiting blocks symmetrically arranged on an end surface of a distal end of the tightening tube; the two limiting blocks are bent inward respectively.

As an improvement of the hemostatic clip with a split structure according to the invention, the third limiting mechanism includes a first limiting hole and a pin; two first limiting holes are symmetrically provided on a side wall of the distal end of the tightening tube; the pin passes through the two first limiting holes respectively, and then is fixed with the tightening tube.

As an improvement of the hemostatic clip with a split structure according to the invention, the fourth limiting mechanism is a second limiting hole provided on a side wall of a proximal end of the tightening tube relative to the barb.

Compared with the prior art, the invention has the following beneficial effects: (1) the split structure simplifies the structure of the parts, reduces manufacturing costs, and solves the problem in the prior art that the principle of "small into large" must be followed during assembly, thereby realizing "fitting in" first and then welding to solving the existing problems in assembly; (2) manufacturing and construction of parts are simplified; (3) functionally, it is exactly the same as the CNC machined part, with complete and quick separation of the clamp part and the release part; (4) after the clip is released and closed, it can be opened and disengaged again.

DETAILED DESCRIPTION OF THE INVENTION

Figure 1:
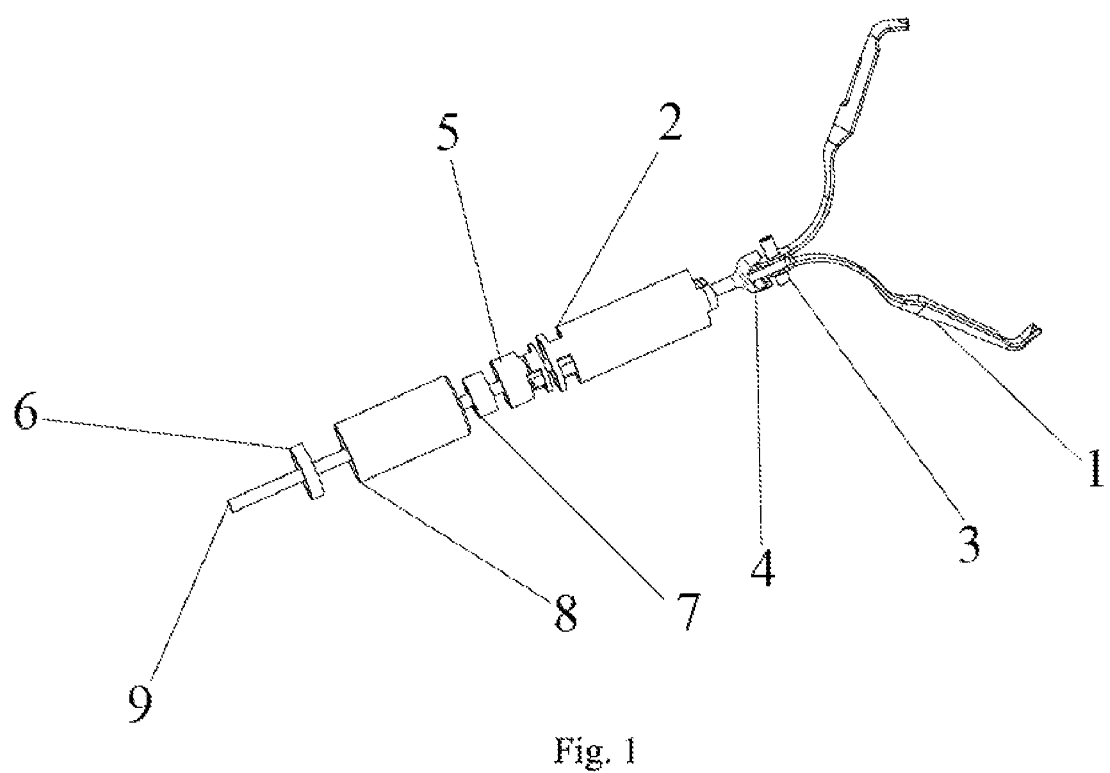
FIG. 1 is a diagram of main structures of the invention.
Figure 2:
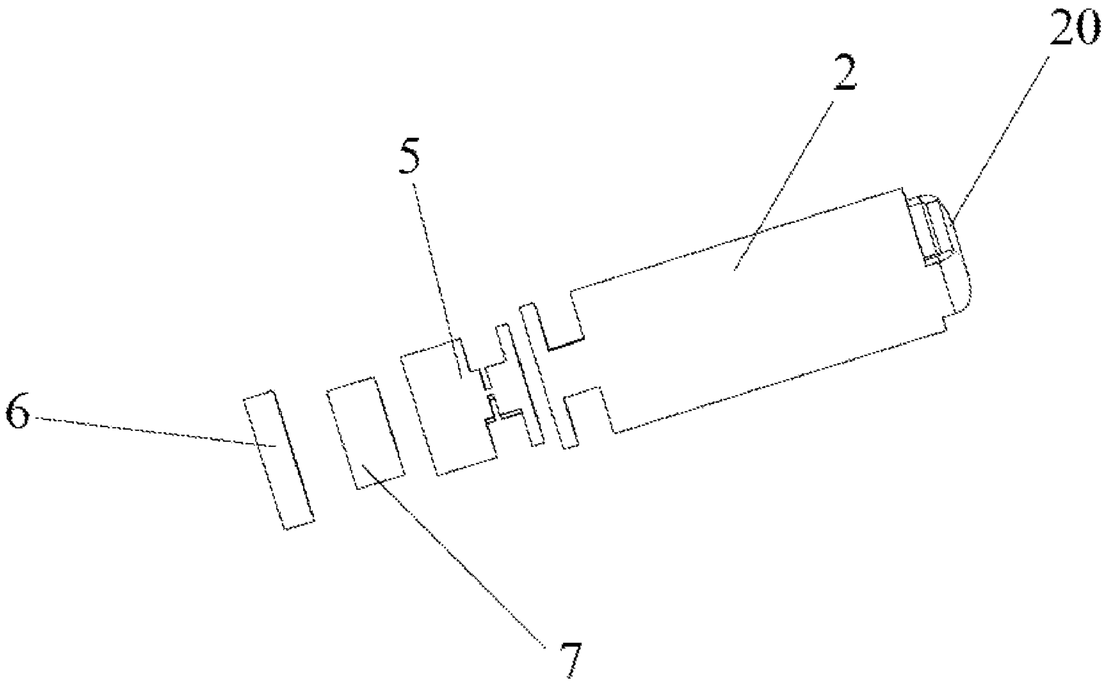
FIG. 2 is a diagram of one structure of a middle ring, an outer connecting ring, an inner connecting ring and a tightening tube in FIG. 1.
Figure 3:
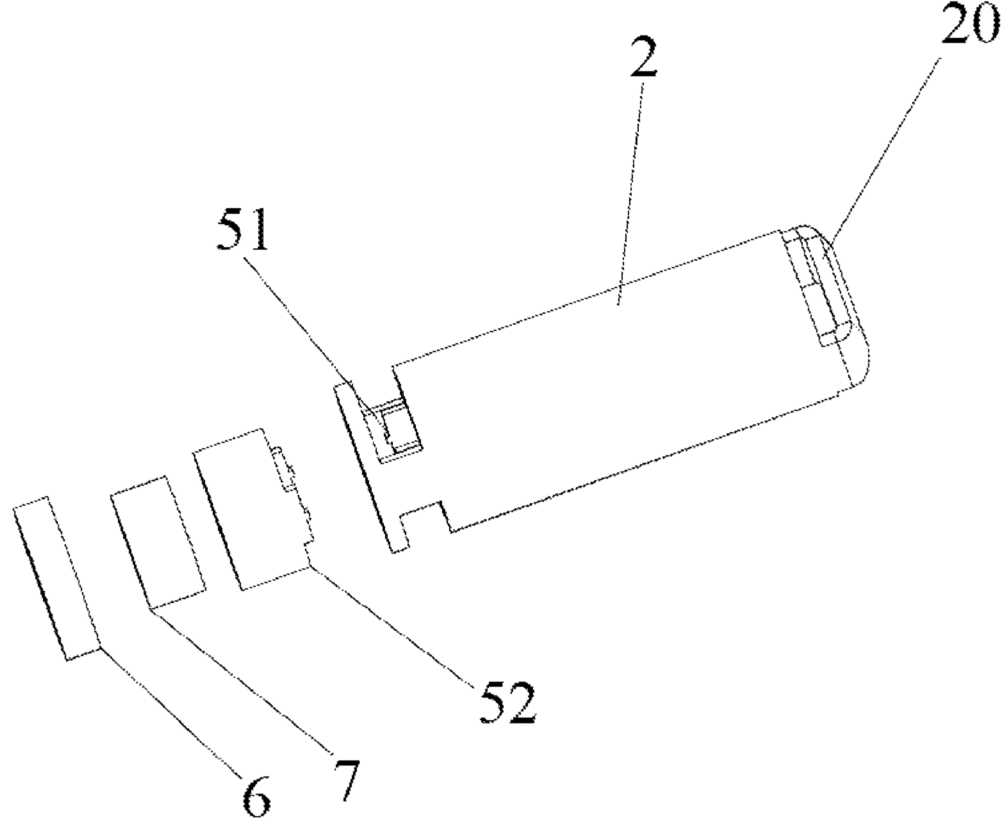
FIG. 3 is a structural diagram after the middle ring in FIG. 2 is released.
Figure 4:
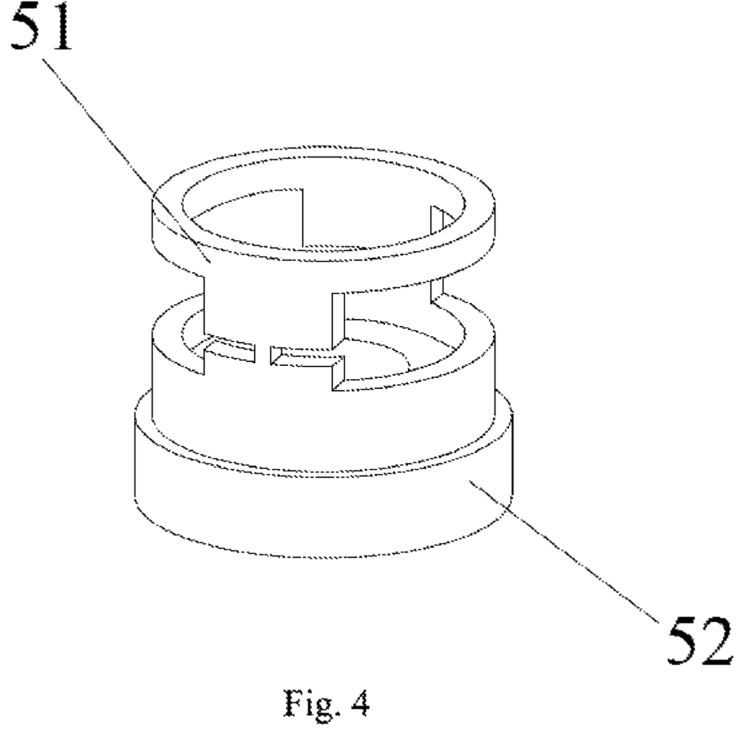
FIG. 4 is a specific structural diagram of the middle ring in FIG. 2.
Figure 5:
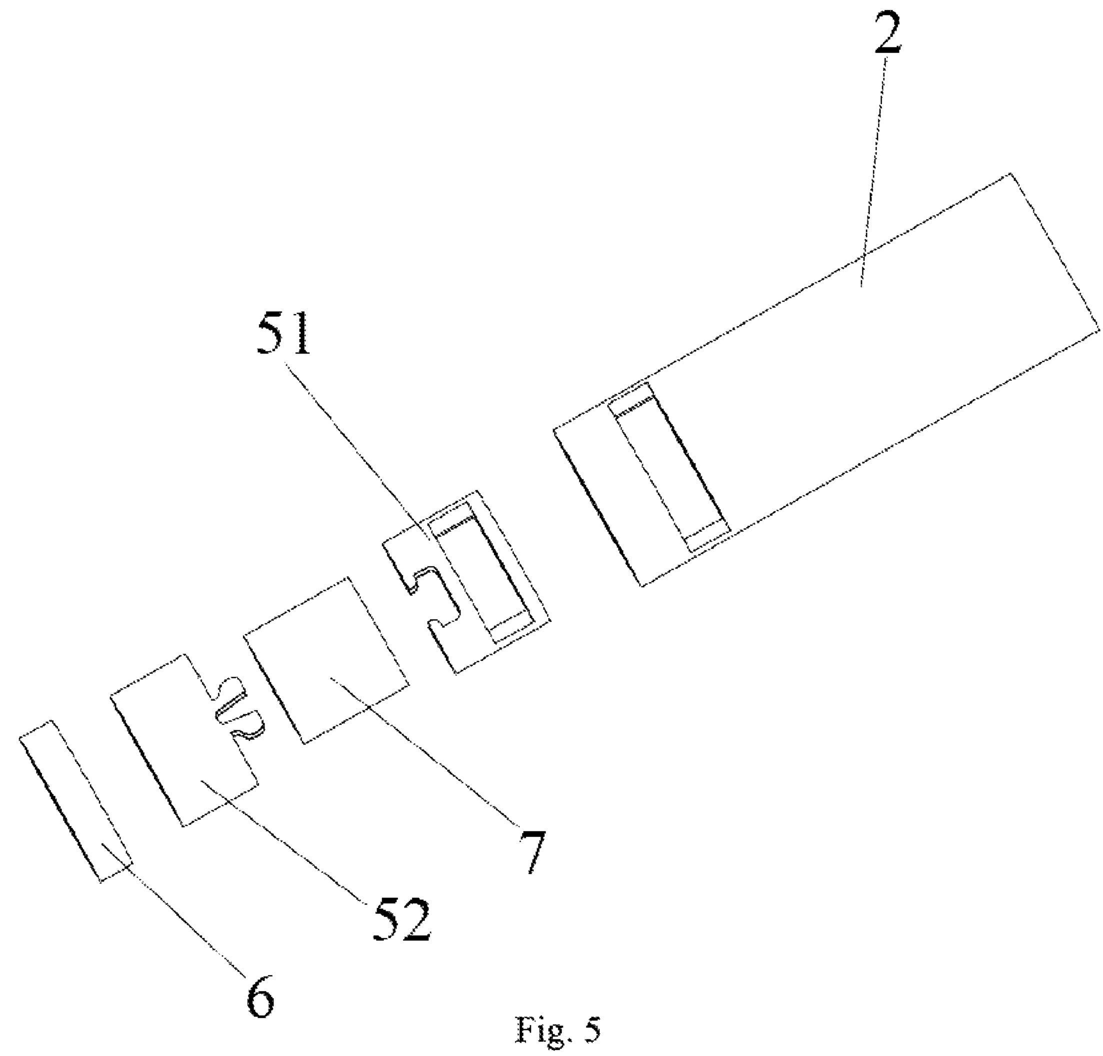
FIG. 5 is a diagram of the other structure of a middle ring, an outer connecting ring, an inner connecting ring and a tightening tube in FIG. 1.
Figure 6:
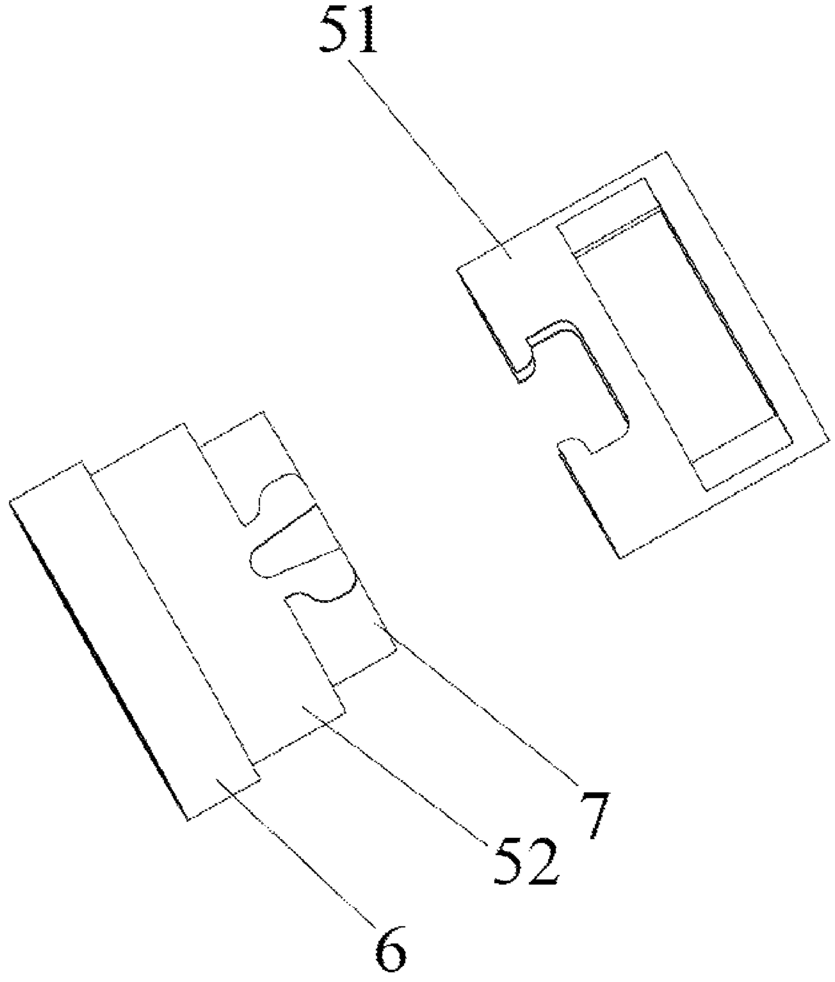
FIG. 6 is a structural diagram after the middle ring in FIG. 5 is released.
Figure 7:
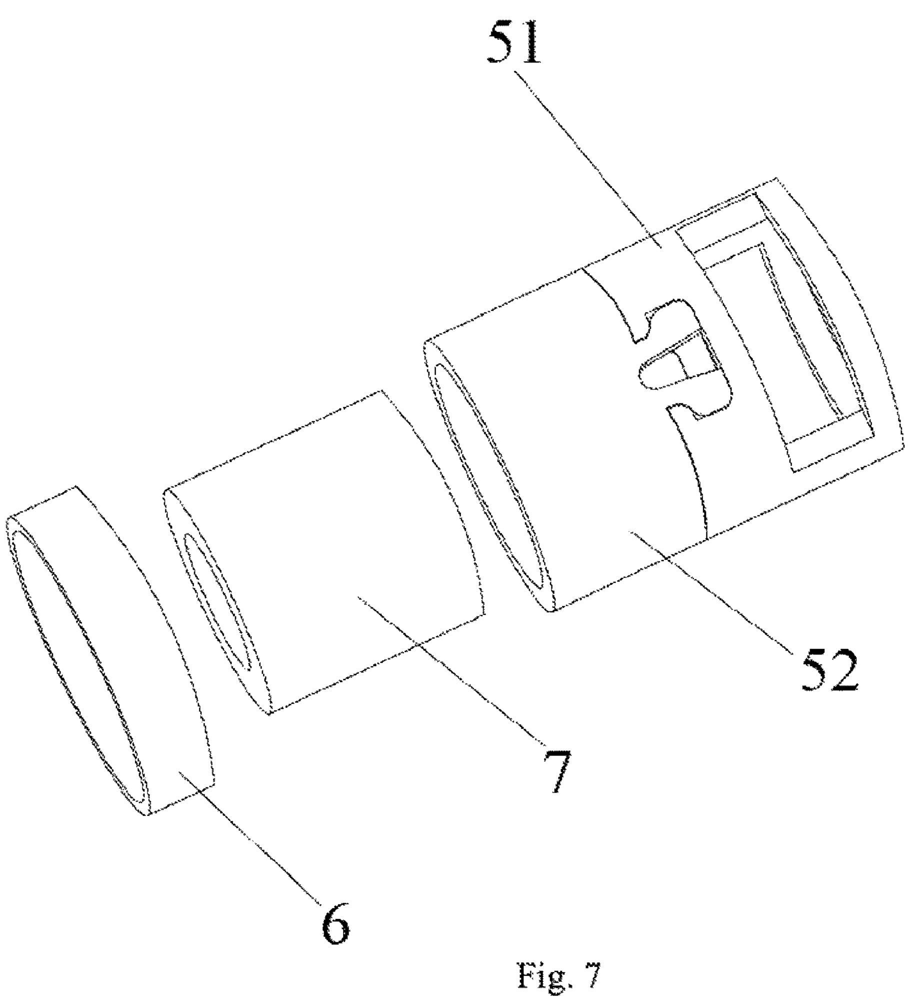
FIG. 7 is a specific structural diagram of the middle ring in FIG. 5.
Figure 8:
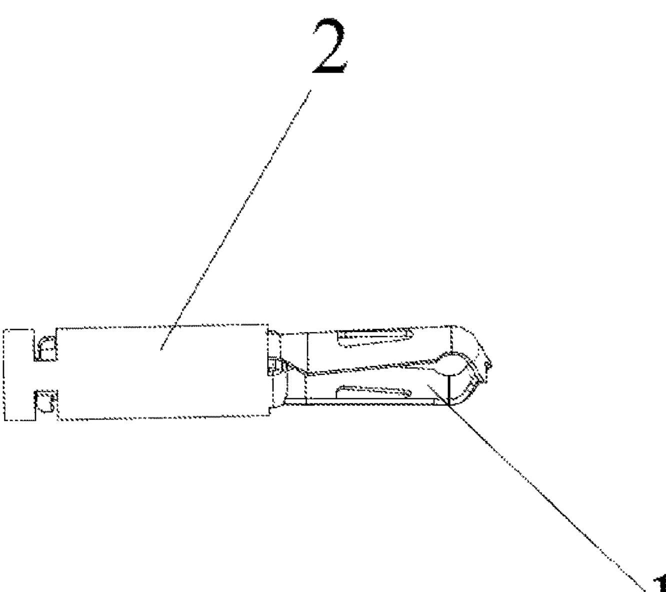
FIG. 8 is a diagram showing a closing state of a clamp in FIG. 1.
Figure 9:
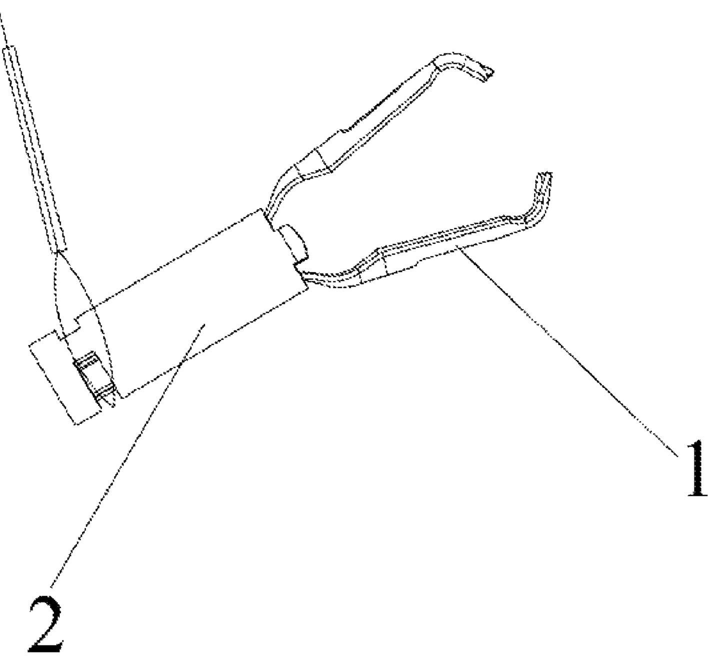
FIG. 9 is a flow chart of opening the clamp in FIG. 8.

Embodiment 1 FIGS. 1 to 9 show a hemostatic clip with a split structure. The hemostatic clip includes a control portion and a releaser; a sliding grip, a handle with a built-in sliding groove, a spring tube, a mandrel 9 (the mandrel 9 is a metal monofilament or a rope), an internal socket 4, and a clamp 1; the releaser includes a middle ring 5, an outer connecting ring 6, an inner connecting ring 7, an outer ring 8, and a tightening tube 2.

The sliding grip is sleeved into the sliding groove of the handle, and a distal end of the sliding grip is fixed to a proximal end of the mandrel 9.

The clamp 1 is two split clamps or two integrated clamps; the embodiment provides a split solution, i.e., two symmetrically arranged clamps 1 form a clip. The above clamp 1 consists of a tail, a rear arm, a forearm, and a claw end in order from left to right. A connection between the tail and the rear arm is provided with a certain arc, and the entire clamp 1 or the connection is made of elastic metal material, so that the opening and closing functions of the clip are realized through the elastic force brought by the curvature of the position when in clamping. The tail is provided with a second hole (the second hole is a connecting hole, connected to the internal socket 4 through a pin 3), and an end portion of the tail is provided with one or two protruding barbs (the barb is a limiter when the clip is closed, and the closing and locking function is realized through a limit hole of the tightening tube 2); the forearm is provided with a first hole (the shape of the first hole may be circular, elliptical, hollow or trapezoidal, etc., and the number of the first holes may be 1 or several), so that with the provision of the mechanism, the expandability of related products of the invention is improved, and linkage with other related devices may be realized through the first hole; a front end of the claw end is provided with teeth I, and the teeth I of the two clamps 1 are in mutual meshing state (for example, one is single-tooth, the other is double-tooth, or the two teeth are in mutual meshing state, which are mainly used for the conventional design of clamping stability).

The tightening tube 2 of the invention is cylindrical, with a hollow interior, forming a cavity that is not sealed at the top or bottom. A distal end of the tightening tube 2 (a clamping portion is the distal end and a handle portion is the proximal end, which, i.e., the position, is defined by a distance from the instrument operator) is provided with a limiting mechanism that restricts the clamp 1 from running out of the tightening tube 2, and the limiting mechanism is composed of two symmetrical limiting blocks 20; the limiting block 20 is bent inward, and after bending, the two gaps formed by the limiting blocks 20 and a port of the distal end of the tightening tube 2 are a position of an extension port of the clamp 1. A proximal end of the tightening tube 2 is provided with a limiting hole, and the limiting hole is a hole dug through a side wall of the tightening tube 2 and penetrating the side wall of the tightening tube 2. Through the elastic force brought by the curvature of the clamp 1, the barbs of the two clamps 1 press against an inner wall of the tightening tube 2, and once the barb reaches the position of the limiting hole, the barb of the barb clamp 1 may be stuck in the limiting hole to limit the movement of the clamp 1 to a distal end.

A middle ring 5 is provided at the proximal end of the tightening tube 2. The middle ring 5 is a cylinder with the same outer diameter as an inner diameter of the tightening tube 2 and is hollow inside. The middle ring 5 includes a middle ring front portion 51 and a middle ring rear portion 52, and the middle ring front portion 51 is sleeved in a proximal tube of the tightening tube 2 and then fixedly connected by welding. A break point is provided between the middle ring front portion 51 and the middle ring rear portion 52 (for example, a break point that may be broken directly within a force of 30 N is cut), and an inner connecting ring 7 is provided on an inner wall of the middle ring rear portion 52 and is then fixedly connected by welding. An outer side wall of the middle ring rear portion 52 is sleeved with an outer connecting ring 6, and is then fixedly connected by welding. The outer connecting ring 6 is located at an inner ring of the outer ring 8, and has a clearance fit with the outer ring 8. An inner side wall of a distal end of the outer ring 8 is provided with protruding limiting blocks (protruding annularly along the inner side wall of the distal end of the outer ring 8), and the limiting blocks may prevent the outer connecting ring 6 from moving radially toward a distal end. An outer diameter of the tightening tube 2 is at least the same as an inner diameter of the outer ring 8, or the outer diameter of the tightening tube 2 is at least the same as an outer diameter of the outer ring 8.

A distal end of the handle and a proximal end of the spring tube are fixed to each other, and a distal end of the spring tube and a proximal end of the outer ring 8 are fixed to each other (in welded fixation); the spring tube is sleeved outside the mandrel 9, and a lower end of the sliding grip and the outer ring 8 are connected with each other through an external protective shell, which is on the outside of the spring tube.

The tails of the two clamps 1 are sleeved into the tightening tube 2 from the distal end of the tightening tube 2. The pin 3 passes through the second hole of the two clamps 1 to combine the two clamps 1, and the two clamps 1 are connected with the internal socket 4 through the pin 3.

A proximal end of the internal socket 4 is provided with a connecting portion that is interconnected with the mandrel 9, and through the connecting portion, a distal end of the mandrel 9 and the proximal end of the internal socket 4 are fixed with each other. A distal end of the internal socket 4 is provided with a connecting portion with the clip. The connecting portion is arranged by two methods. One of the two methods is to provide protruding C-shaped holes at the distal end of the internal socket 4 and to provide protective wings on both sides of the protruding C-shaped hole, wherein an opening of a notch of the C-shaped hole faces the distal end. Compared with the solution in the prior art of providing C-shaped holes on the clip, the technical solution of the invention is more stable when achieving separation, because there is no fixing mechanism between the two clamps of the clip so that the clamps are easy to fall apart after the C-shaped holes of the clip are separated; through the technical improvement of the invention, the above possible risk is completely eliminated.

After the pin 3 is used to insert the second hole and the C-shaped hole at the tail of the clamp 1 in sequence, the clamp 1 may be connected with the internal socket 4. The pin 3 may also be a solid rod or a straight tube (or a straight solid rivet or a hollow rivet). The clamp 1 is contracted within the tightening tube 2 in a closing state.

In actual operation, the barbs at the tails of the two clamps 1 may be limited by two or more symmetrical limiting holes that prevent the clamps from moving forward provided at a tail of the tightening tube 2, and once the barbs at the tails of the two clamps 1 are pulled to the position of the limiting holes, the barbs will hang on the holes; since the two clamps 1 are made of elastic metal, the elastic force brought by the curvature cooperates with the inner cavity of the tightening tube 2 to complete the clamping function, and further the fixation is completed through the limiting function of the limiting hole.

The radial movement of the two clamps 1 is completed by sliding the grip to control the mandrel 9; the sliding grip controls the front and rear radial movement of the mandrel 9, the mandrel 9 controls the internal socket 4, and the internal socket 4 drives the two clamps 1. Due to the inner connecting ring 7 provided on an inner ring of the middle ring rear portion 52, the internal socket 4 is stuck in the position of the inner connecting ring 7 when moving radially toward a proximal end; then, the internal socket 4 drives the inner connecting ring 7 to move radially toward a proximal end, the inner connecting ring 7 drives the middle ring 5 to move radially toward a proximal end, and the middle ring 5 drives the outer connecting ring 6 to move radially toward a proximal end, and then the tightening tube 2 is stuck at one side of the outer ring 8. Therefore, when the middle ring 5 moves radially toward a proximal end, once the tightening tube 2 gets stuck at one side of the outer ring 8, further radial movement toward a proximal end may not be realized; then, when a force exceeding 30 N is applied, the internal socket 4 is stressed, the middle ring front portion 51 and the middle ring rear portion 52 are broken and separated from each other due to the blocking of the inner connecting ring 7 (the middle ring front portion 51 is welded and fixed to the tightening tube 2, and the inner connecting ring 7 inside the middle ring rear portion 52 blocks the internal socket 4), and the protruding barbs of the clamps are stuck into the limiting holes at the proximal end of the tightening tube 2.

The outer ring 8 is an intermediate body connecting the spring tube and the clamping portion, and the outer ring 8 and the spring tube are welded together.

When in assembly, the first method is as follows:

the inner connecting ring 7 is welded on an inner side surface of the middle ring rear portion 52;

the outer connecting ring 6 welded on an outer side surface of the middle ring rear portion 52;

the middle ring 5 is sleeved into the outer ring 8 from the proximal end of the outer ring 8;

an end surface of a front end of the middle ring front portion 51 is welded with an end surface of a rear end of the tightening tube 2;

the outer ring 8 is welded with the spring tube.

When in assembly, the second method is as follows:

welding holes are reserved on the outer ring 8;

the inner connecting ring 7 is welded on an inner side surface of the middle ring rear portion 52;

the middle ring 5 is sleeved into the outer ring 8 from the distal end of the outer ring 8;

the outer connecting ring 6 is sleeved into the outer ring 8 from the proximal end of the outer ring 8;

through the welding holes reserved on the outer ring 8, the outer connecting ring 6 welded on an outer side surface of the middle ring rear portion 52;

the outer ring 8 is welded with the spring tube.

Embodiment 2 The limiting mechanism of the tightening tube 2 described in Embodiment 1 is a pin. Holes are made at a front end of the tightening tube 2, a transverse pin is inserted, and a port at the front end of the tightening tube 2 is divided into two parts through the pins, which serve as the detection ports of the clamp 1 respectively.

Embodiment 3 The distal end of the internal socket 4 described in Embodiment 1 is provided with two symmetrical protective wings, and a C-shaped hole with a notch opening upward is provided on the protective wings.

Embodiment 4 The middle ring front portion 51 is provided with a C-shaped port; relative to the C-shaped port, a V-shaped elastic piece is provided at the middle ring rear portion 52; an opening position of the V-shaped elastic piece is inserted into the C-shaped port.

Embodiment 5 The middle ring rear portion 52 is provided with a C-shaped port; relative to the C-shaped port, a V-shaped elastic piece is provided at the middle ring front portion 51; an opening position of the V-shaped elastic piece is inserted into the C-shaped port.

Finally, it should also be noted that the above enumeration is only a specific embodiment of the invention. Obviously, the invention is not limited to the above embodiments, and many modifications are possible. All modifications that those skilled in the art can directly derive or associate from the disclosure of the invention should be considered to be within the protection scope of the invention.

The invention claimed is:

1. A hemostatic clip with a split structure, comprising a control portion and releaser, the control portion comprising a grip, a handle, a spring tube, a mandrel, a clamp with a barb at the end and an internal socket, the grip being connected with the mandrel, wherein the releaser comprises a middle ring and an outer ring;

the handle is connected with the outer ring through the spring tube;

the outer ring is sleeved on the outside of the middle ring;

an inner side of the outer ring and an outer side of the middle ring are provided with a first limiting mechanism that limits a radial movement of the middle ring toward a proximal end;

the middle ring is provided with a tightening tube;

a distal end of the mandrel passes through the outer ring, the middle ring and the tightening tube in sequence, and then is connected with the clamp through the internal socket;

the internal socket and the clamp are located in the tightening tube; and inside the middle ring is provided a second limiting mechanism that limits a radial movement of the internal socket toward the proximal end.

2. The hemostatic clip with a split structure according to claim 1, wherein the middle ring comprises a middle ring front portion and a middle ring rear portion;

an inner side of the middle ring front portion is provided with an inner connecting ring to form the first limiting mechanism;

an outer side of the middle ring front portion is provided with an outer connecting ring, which forms the second limiting mechanism together with a protrusion provided on an inner side of a proximal end of the outer ring;

the middle ring rear portion is fixedly connected with the tightening tube.

3. The hemostatic clip with a split structure according to claim 2, wherein a maximum force of 30 N may be withstood between the middle ring front portion and the middle ring portion.

4. The hemostatic clip with a split structure according to claim 2, wherein the middle ring front portion is provided with a C-shaped port;

relative to the C-shaped port, a V-shaped elastic piece is provided at the middle ring rear portion;

an opening position of the V-shaped elastic piece is inserted into the C-shaped port.

5. The hemostatic clip with a split structure according to claim 2, wherein the middle ring rear portion is provided with a C-shaped port;

relative to the C-shaped port, a V-shaped elastic piece is provided at the middle ring front portion;

an opening position of the V-shaped elastic piece is inserted into the C-shaped port.

6. The hemostatic clip with a split structure according to claim 1, wherein the tightening tube is of a cylindrical structure with a hollow center, which has a distal end provided with a third limiting mechanism that limits the clamp from running out and a proximal end provided with a fourth limiting mechanism that limits a position of the clamp after clamping.

7. The hemostatic clip with a split structure according to claim 6, wherein the third limiting mechanism is two limiting blocks symmetrically arranged on an end surface of a distal end of the tightening tube;

the two limiting blocks are bent inward respectively.

8. The hemostatic clip with a split structure according to claim 6, wherein the third limiting mechanism comprises a first limiting hole and a pin;

two first limiting holes are symmetrically provided on a side wall of the distal end of the tightening tube;

the pin passes through the two first limiting holes respectively, and then is fixed with the tightening tube.

9. The hemostatic clip with a split structure according to claim 6, wherein the fourth limiting mechanism is a second limiting hole provided on a side wall of a proximal end of the tightening tube relative to the barb.

* * * * *